United States Patent [19]

Young et al.

[11] Patent Number: 5,068,469
[45] Date of Patent: Nov. 26, 1991

[54] PROCESS FOR PREPARATION OF CONDENSED ALCOHOLS BY ALKOXIDE CATALYSTS

[75] Inventors: David A. Young; John A. Jung; Mark L. McLaughlin, all of Baton Rouge, La.

[73] Assignee: Exxon Chemical Patents Inc., Linden, N.J.

[21] Appl. No.: 476,163

[22] Filed: Feb. 7, 1990

[51] Int. Cl.$^5$ .................... C07C 29/34; C07C 31/125
[52] U.S. Cl. ...................................... 568/878; 568/905
[58] Field of Search ............................... 568/878, 905

[56] References Cited

U.S. PATENT DOCUMENTS

| | | | |
|---|---|---|---|
| 1,992,480 | 2/1935 | Fuchs et al. | 568/905 |
| 2,457,866 | 1/1949 | Carter | 260/642 |
| 2,762,847 | 9/1956 | Miller et al. | 260/642 |
| 2,836,628 | 5/1958 | Miller | 568/905 |
| 2,862,013 | 11/1958 | Miller et al. | 260/410.9 |
| 3,119,880 | 1/1964 | Kollar et al. | 260/642 |
| 3,328,470 | 6/1967 | Poe | 568/905 |
| 3,514,493 | 5/1970 | Pregaglia et al. | 260/642 |
| 3,544,635 | 12/1970 | Kehoe et al. | 568/909 |
| 3,558,716 | 1/1971 | Englehardt et al. | 568/905 |
| 3,860,664 | 1/1975 | Yates | 260/642 C |
| 3,916,015 | 10/1975 | Yates | 260/642 C |
| 4,518,810 | 5/1985 | Matsuda et al. | 568/905 |
| 4,590,314 | 5/1986 | Kinkade | 568/909 |
| 4,681,868 | 7/1987 | Budge et al. | 568/905 |

OTHER PUBLICATIONS

Liubomilou et al., "Bulletin Izobreteniy", 1959, No. 7, p. 10, (U.S.S.R.).
Pratt et al., "J. Am. Chem. Soc.", vol. 75 (1954), pp. 52-56.
S. Veibel et al., Tetrahedron, 1967, vol. 23, pp. 1723-1733, "On the Mechanism of the Guerbet Reaction".
G. Gregorio et al., Journal of Organometallic Chemistry, 37 (1972), pp. 385-387, "Condensation of Alcohols Catalysed by Tertiary Phosphine Transition Metal Complexes".
P. L. Burk et al., Journal of Molecular Catalysis, 33 (1985), pp. 1-14, "The Rhodium-Promoted Guerbet Reaction Part I. Higher Alcohols from Lower Alcohols".

*Primary Examiner*—J. E. Evans
*Attorney, Agent, or Firm*—J. J. Mahon

[57] ABSTRACT

Condensed dimer alcohols, also known as Guerbet alcohols, are prepared using metal alkoxide as the catalyst by reacting alcohol with saturated or unsaturated aldehyde or allyl alcohol, or mixtures thereof, at 100°-220° C. and removing water as it is formed during the reaction. Dimer alcohols are prepared in high yields without the need for a transition metal catalyst.

5 Claims, No Drawings

PROCESS FOR PREPARATION OF CONDENSED ALCOHOLS BY ALKOXIDE CATALYSTS

This invention relates to the preparation of branched dimerized or condensed alcohols, which are known as Guerbet alcohols. More particularly, this invention relates to the preparation of such alcohols using a metal alkoxide as the sole catalyst.

The Guerbet reaction for the preparation of condensed alcohols is well known in the art. In this reaction, a primary or secondary alcohol which has a methylene group adjacent to the hydroxylated carbon atom, i.e., an alcohol of the formula $RCH_2CH_2OH$, is condensed with an alcohol of a similar structure to provide a condensed or dimer alcohol which contains the total carbon atoms of the two alcohol reactants.

Numerous references disclose the use of various transition metal catalysts and co-catalysts to prepare the desired Guerbet alcohol product. Representative disclosures include U.S. Pat. No. 2,457,866, which discloses alkali condensation catalysts and dehydrogenation catalysts; U.S. Pat. No. 2,762,847, which uses phosphate catalysts; U.S. Pat. No. 2,862,013, which requires an inorganic base and a dehydrogenation catalyst; U.S. Pat. No. 3,119,880, which discloses an alkali and a lead salt, preferably with a dehydrogenation catalyst; U.S. Pat. No. 3,514,493, which teaches the use of an alkaline condensing agent and a platinum, palladium, ruthenium or rhodium catalyst; U.S. Pat. No. 3,860,664, which employs an alkali metal catalyst in combination with certain palladium compounds; U.S. Pat. No. 4,518,810, which discloses a copper-nickel catalyst in combination with an alkaline substance and U.S. Pat. No. 3,916,015, which discloses the use of organic zinc salts of carboxylic acids, beta-diketones and sulfonic acids.

The mechanism of the metal catalyzed Guerbet reaction has been studied by Veibel et al. in Tetrahedron, 1967, Vol. 23, pp. 1723–1733, by Gregorio et al. in Journal of Organometallic Chemistry 37 (1972), pp. 385–387, and by Burk et al. in Journal of Molecular Catalysis 33 (1985), pp. 1–14. Each of these references note the presence of aldehyde in the various metal catalyzed systems which were studied but do not recognize that Guerbet alcohol can be formed in high yields in the absence of a transition metal catalyst.

The present invention is distinct from the prior art in that it effectively prepares condensed alcohols at high yields in the absence of the need for any transition metal catalyst. This invention is based upon the discovery that Guerbet alcohols can be prepared from a mixture of alcohols and aldehydes, saturated or unsaturated, or a mixture of alcohols, aldehydes and allyl alcohols, or a mixture of alcohols and allyl alcohols, utilizing only a metal alkoxide as the sole catalyst. Eliminating the need for a transition metal catalyst is a substantial advantage.

It should also be noted that the present invention allows operations at temperatures significantly lower than those commonly employed in the uncatalyzed Guerbet reaction which are typically 250°-300° C.; the present process operates in the range of 100°-220° C.

In accordance with the present invention, there has been discovered a process for preparing condensed, saturated dimer alcohols having alkyl branching in the 2 position and being represented by the formula $RCH(R)CH_2OH$ which comprises contacting an alcohol reactant of the formula $RCH_2CH_2OH$ with (i) a saturated aldehyde of the formula $RCHO$, or with (ii) an unsaturated aldehyde of the formula $RCH=C(R)CHO$, or with (iii) an allyl alcohol of the formula $RCH=C(R)CH_2OH$, or with mixtures of two or more of (i), (ii) and (iii) in the presence of a metal alkoxide as the sole required catalyst at a temperature of about 100° to 220° C. and removing water as it is formed during the course of the reaction, wherein R represents $C_1$–$C_{20}$ alkyl and the alkoxide has 1 to 20 carbon atoms, and recovering therefrom said dimer alcohol product.

This invention is based upon the discovery that the following reactions are occurring in the reaction system of the present invention:

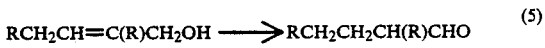

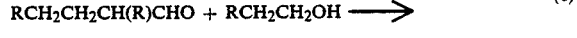

The foregoing equations illustrate the essential aspects of the present invention:
(a) Equation (2) shows that alkoxide catalysis forms an unsaturated aldehyde which is driven to completion by water removal;
(b) Equation (3) shows that alkoxide catalysis reduces the unsaturated aldehyde dimer and produces allyl dimer alcohol and monomer aldehyde;
(c) Equation (4) shows that alkoxide catalysis reduces the unsaturated aldehyde dimer and produces saturated dimer aldehyde and monomer aldehyde;
(d) Equation (5) shows isomerization of allyl alcohol dimer to saturated dimer aldehyde, the reaction being catalyzed by alkoxide;
(e) Equation (6) shows that saturated dimer aldehyde is reduced and monomer alcohol feed reactant is oxidized in an alkoxide catalyzed reaction to produce the desired saturated dimer Guerbet alcohol product and monomer aldehyde.

Equation (1) shows in situ formation of alkoxide and Equation (7) shows by-product ester formation.

It should be emphasized that the addition of aldehyde, allyl alcohol and/or unsaturated aldehyde is instrumental in driving the condensation of primary alcohol monomer to the desired dimer alcohol product.

The present invention applies generally to the use of alcohol, aldehyde, or allyl alcohol reactants which have 3 to about 20 carbon atoms. Suitable alcohols may be generally defined by the formula $RCH_2CH_2OH$, wherein R is a $C_1$–$C_{20}$ alkyl group. Preferred for use in the present invention are alcohol and aldehyde reactants derived from the oxo process which are those $C_6$ to $C_{17}$ alcohols and aldehydes produced by hydroformylation of olefins and which contain branched chain primary alcohols such as branched chain oxo octyl alcohols or branched chain decyl alcohols, but about 20% of said alcohols will also have branching in the 2- position and these cannot be condensed in a Guerbet-type reaction.

The present invention is also applicable to prepare condensed alcohols derived from reactants which have different numbers of carbon atoms. The alkoxide, primary alcohol, allyl alcohol, saturated or unsaturated aldehyde may each have carbon atoms ranging from 3 to 20 carbon atoms and corresponding statistical distributions of products may be obtained.

The metal alkoxide may be a potassium, lithium, sodium, cesium, magnesium, calcium, strontium, aluminum, gallium or rubidium alkoxide, with potassium being preferred. It may be formed in situ by first reacting a metal hydroxide with the $RCH_2CH_2OH$ reactant.

The quantity of metal alkoxide used may generally be expressed as about 1 to 15 wt.%, based on the weight of primary alcohol initially present in the reaction mixture, the preferred amount being about 2 to 12 wt.% alkoxide.

To prepare the preferred products, which are the dimers of the primary alcohol reactant, the alkoxide should be prepared from the primary alcohol reactant. If the alkoxide is prepared from a different chain length material, then mixed products of different carbon atom number will be prepared, but such products and processes are within the scope of the present invention.

In practicing the process of this invention the alcohol, aldehyde and/or allyl alcohol are admixed and combined with the metal alkoxide and the reaction mixture is heated to a temperature of about 100° C. to 220° C. to initiate the reaction. Water should be removed as rapidly as possible as soon as it is formed and normally this method of removal will be by distillation of an azeotropic mixture of water and alcohol or a azeotropic mixture of water and other materials present in the feedstock, such as unreacted olefins and alkanes which are present in the system when the feedstock is a mixture of alcohols and aldehydes taken from the oxo process. Water is removed at the appropriate reflux temperature, which is a function of the types of reactants introduced into the reaction vessel. Water removal may also be effected by vacuum or the use of an inert gas purge or sweep of the system.

Use of a reaction system comprising primary alcohol, saturated aldehyde and potassium alkoxide represents a preferred embodiment of this invention. The aldehyde and alcohol are initially present in approximately equimolar amounts, but an alternative procedure is to periodically add aldehyde to the heated reaction mixture of alcohol and alkoxide over a period of time. This incremental addition of aldehyde will minimize the reaction shown in Equation (7) above, which produces by-product heavy ester products.

In carrying out the process of the invention utilizing incremental addition of the aldehyde, the amount of aldehyde addition is controlled so that there is present in the reaction mixture about 5-15 mole % of aldehyde based on the total moles of primary alcohol and aldehyde. Thus the process may be operated in a continuous manner through controlled aldehyde addition so that the aldehyde content is maintained at the 5-15 mole % level.

The present invention will generally result in yields of dimer alcohol in the range of about 70 to 95%, based upon the quantity of condensable alcohols present in the reaction mixture.

A particularly preferred embodiment of the present invention comprises conducting the reaction utilizing an oxo process product mixture as the reactant. Such products contain mixtures of primary alcohols, aldehydes and light and heavy oxo product fractions. The oxo process refers to the hycroformylation of olefins to produce mixtures of branched chain primary alcohols which also contain about 20% by weight of alcohols branched in the 2- position. The crude oxo product mixture also contains aldehydes, unreacted light olefins, saturated alkanes and complex mixed heavy oxo fractions. The present invention is particularly useful in preparing primary dimer alcohols from oxo products containing $C_6$ to $C_{13}$ oxo alcohols and aldehydes.

The invention is further illustrated by the following examples which are not to be considered as limitative of its scope.

EXAMPLE 1

(a) A solution of potassium octyl alkoxide was prepared by combining, under nitrogen, 35.0 g. of 85% KOH pellets and 500.0 g. of 1-octanol and heating and stirring the mixture while the pellets dissolved. Water was removed azeotropically over 3 hours as the reaction mixture temperature was raised from 130° C. to 190° C., and a total of 14.4 g. water was removed. The product alkoxide solution was stored under nitrogen; 526.0 g. (613 ml.) was prepared.

(b) A 250 ml., three necked round bottom flask fitted with a distillation head, nitrogen inlet, stirrer and thermometer was charged, under nitrogen, with 60 ml. of the alkoxide solution prepared in (a) and heated with stirring to 170° C. 10 ml., 9.6 g., of 1-octanal was injected into the flask. After 3 minutes the temperature rose to 180° C. and Sample No. 1 was taken. Over the next 6 minutes, the reaction mixture temperature was raised to 194° C. and refluxing began; over the next 14 minutes the reaction mixture temperature was raised to 207° C. and 0.7 g. of water was azeotropically distilled off and then Sample No. 2 was taken. Each sample was analyzed:

| Sample No. 1 Analysis: | |
|---|---|
| 1-octanal | 0.11 wt. % |
| 1-octanol | 75.51 wt. % |
| octanoic acid | 1.00 wt. % |
| $C_{16}$ unsaturated alcohol dimer aldehyde and allyl alcohol dimer | 8.33 wt. % |
| $C_{16}$ saturated dimer alcohol | 5.62 wt. % |
| $C_{24}$ ester trimers | 1.40 wt. % |
| $C_{32}$ ester tetramers | 6.92 wt. % |
| Sample No. 2 Analysis: | |
| 1-octanol | 58.56 wt. % |
| $C_{16}$ unsaturated alcohol dimers aldehyde and allyl alcohol dimers | 6.30 wt. % |
| $C_{16}$ saturated dimer alcohol | 21.40 wt. % |
| $C_{24}$ ester trimers | 1.96 wt. % |
| $C_{32}$ ester tetramers | 8.80 wt. % |

The desired product, a $C_{16}$ alcohol, is underlined; it has the formula $R^1(CHR^2)CH_2OH$, wherein $R^1$ is $C_6$ alkyl and $R^2$ is $C_8$ alkyl.

EXAMPLE 2

Using a 500 ml. flask fitted as in the previous example, 265 ml., 234.2 g., of a de-cobalted (cobalt oxo catalyst removed) oxo process product resulting from the hydroformylation of branched internal $C_9$ olefin isomers was charged to the flask under nitrogen. The feed analyzed as follows:

| | |
|---|---|
| Unreacted $C_9$ olefins and alkanes | 22.35 wt. % |
| $C_{10}$ branched aldehydes | 35.89 wt. % |
| $C_{10}$ branched alcohols | 40.26 wt. % |
| Heavy oxo fraction | 1.50 wt. % |

To this reaction mixture was added 17.1 g. of 85% KOH pellets with stirring and the mixture was heated to 103° C. until all pellets dissolved, thereby forming alkoxide. Refluxing started when the reaction temperature reached 157° C. Over the next 77 minutes 9.9 g. of water was removed by azeotropic distillation as the temperature was increased to 194° C. A sample was then taken which analyzed as follows:

| | |
|---|---|
| Unreacted $C_9$ olefins and alkanes | 24.38 wt. % |
| $C_{10}$ alcohols | 16.19 wt. % |
| $C_{10}$ carboxylic acids | 3.14 wt. % |
| $C_{20}$ saturated dimer alcohol | 32.05 wt. % |
| Heavy esters and heavy oxo product | 24.13 wt. % |

The $C_{20}$ saturated dimer alcohols are the desired products.

EXAMPLE 3

The process of the invention was carried out by adding over a period of three hours 600 g. demetalled oxo product containing 34% $C_{10}$ isoalcohol, 25% $C_{10}$ isoaldehyde, 25% heavies and 12% lights to a solution of potassium alkoxide in 600 g. isodecyl alcohol (12.5% alkoxide) at 200° C. with stirring and with a rapid nitrogen sparge. After about 5 hours, 59.2% of the total alcohol and aldehyde (52.0% of the alcohol) was converted to products. Eighty nine percent of the products was isoeicosyl alcohol ($C_{20}$) with some unsaturated isoeicosyl alcohol, 4.1% isodecanoic acid and 6.8% heavy material.

EXAMPLE 4

Another example of the process of the invention was carried out following the procedure of the previous example except that 300 g. demetalled oxo product was added to 900 g. isodecyl alcohol containing 10% potassium alkoxide over a period of three hours at 200° C. and reduced nitrogen sparge. After a total of about 5 hours, 48% of the isodecyl alcohol and isoaldehyde was converted to products, 90% of which was isoeicosyl alcohol.

EXAMPLE 5

In another example, 110 g. of demetalled oxo product was added to 1100 g. isodecyl alcohol containing 11.0% potassium alkoxide over a period of 3 hours at 700° C. and reduced nitrogen sparge. After 5 hours, 20% of the isodecyl alcohol and isoaldehyde was converted to products, most of which was isoeicosyl alcohol.

EXAMPLE 6

This example illustrates that an aldehyde which is not capable of condensation, e.g., 2-ethyl-1-hexanal, may be used to effect the condensation of a primary alcohol, in this case hexanol. This example is presented only to illustrate this principle; the reaction was stopped before the highest possible yields of desired $C_{12}$ dimer alcohol could be obtained.

(a) A three liter, three necked round bottom flask was fitted with a distillation head, nitrogen inlet stopcock attached to a nitrogen source and by-pass bubbler, thermometer and magnetic stirring bar. The flask was charged under nitrogen with 700 ml., 569.8 g., of 1-hexanol and 34.19 g. of 85% potassium hydroxide pellets. The mixture was stirred and heated while the pellets dissolved. Water was removed azeotropically over 2.5 hours as the pot temperature was raised from 138° to 163° C. The head temperature rose from 25° to 156° C. over this time as 14.6 g. of water was removed. The resulting solution of potassium hexyl alkoxide in 1-hexanol, 688 ml., 589.4 g., was cooled to room temperature and stored under nitrogen.

(b) A 250 ml. three necked, round bottom flask was fitted as the flask described above. 100 ml. of the above solution was transferred under nitrogen to this flask. This solution was then heated with stirring to reflux with a pot temperature of 157° C. and a head temperature of 150° C. 20 ml. of 2-ethyl-1-hexanal was then injected into the flask. After six minutes 1.1 g. of water had been removed azeotropically and Sample No. 1 was taken. After 1 hour total time 1.5 g. water had been removed and Sample No. 2 was taken. The reaction was then stopped by cooling.

| Sample No. 1 Analysis: | | |
|---|---|---|
| (a) | 1-hexanol | 64.56 wt. % |
| (b) | 2-ethyl-1-hexanol | 14.35 wt. % |
| (c) | 2-ethyl-1-hexanoic acid, recovered from K salt | 0.62 wt. % |
| (d) | $C_{12}$ dimer allyl alcohols and saturated dimer alcohols formed from 1-hexanol via 1-hexanal intermediate | 6.94 wt. % |
| (e) | $C_{14}$ crossed dimer alcohols and saturated dimer alcohols formed from 1-hexanol via 1-hexanal and 2-ethyl-hexanal intermediates | 3.80 wt. % |
| (f) | $C_{12}$ and $C_{14}$ Tischenko dimer esters | 2.04 wt. % |
| (g) | $C_{16}$ to $C_{20}$ Tischenko dimer and trimer esters formed from 1-hexanal and 2-ethyl-1-hexanal intermediates | 4.76 wt. % |
| (h) | 2-ethyl-1-hexanal | <0.03 wt. % |
| Sample No. 2 Analysis: | | |
| (a) | 1-hexanol | 61.67 wt. % |
| (b) | 2-ethyl-1-hexanol | 14.65 wt. % |
| (c) | 2-ethyl-1-hexanoic acid, recovered from K salt | Not Analyzed |
| (d) | $C_{12}$ dimer allyl alcohols and saturated dimer alcohols formed from 1-hexanol via 1-hexanal intermediate | 10.28 wt. % |
| (e) | $C_{14}$ crossed dimer alcohols and saturated dimer alcohols formed from 1-hexanol via 1-hexanal and 2-ethyl-hexanal intermediates | 4.51 wt. % |
| (f) | $C_{12}$ and $C_{14}$ Tischenko dimer esters | 1.87 wt. % |
| (g) | $C_{16}$ to $C_{20}$ Tischenko dimer and trimer esters formed from 1-hexanal and 2-ethyl-1-hexanal intermediates | 3.88 wt. % |
| (h) | 2-ethyl-1-hexanal | Not Detectable |

These results show that the reaction proceeded as indicated by item (a), a hexanol analysis of 61.67 wt.% and item (d) which shows a dimer alcohol level of 10.28 wt.%.

What is claimed is:

1. A process for preparing a condensed, saturated dimer alcohol having alkyl branching in the 2- position and being represented by the formula $RCH(R)CH_2OH$ which comprises contacting a primary alcohol reactant of the formula $RCH_2CH_2OH$ with a saturated aldehyde of the formula RCHO in the presence of a metal alkoxide at a temperature of about 100° to 220° C., wherein the metal may be potassium, lithium, sodium, rubidium, cesium, magnesium, calcium, strontium, aluminum or gallium and removing water as it is formed during the course of the reaction and recovering therefrom said dimer alcohol, wherein R is alkyl, the alkoxide has 1 to 20 carbon atoms, the primary alcohol and aldehyde having 6 to 17 carbon atoms, the aldehyde being incrementally added to the mixture of alkoxide and primary alcohol so that there is continuously maintained in the reaction mixture about 5–15 mole % of aldehyde based on the total moles of primary alcohol and aldehyde.

2. The process of claim 1 wherein the metal alkoxide is potassium alkoxide.

3. The process of claim 1 or claim 2 wherein the alkoxide is formed in situ by reacting metal hydroxide with the primary alcohol reactant and removing water therefrom.

4. The process of claim 1 wherein both said aldehyde and primary alcohol have the same number of carbon atoms.

5. The process of claim 1 wherein the water is removed by distillation of an azeotropic mixture containing said water.

* * * * *